United States Patent
Segal

(10) Patent No.: US 6,533,578 B2
(45) Date of Patent: *Mar. 18, 2003

(54) DENTAL APPARATUS

(76) Inventor: Alan Julian Segal, 13 Park Avenue, Hale, Cheshire (GB), WA15 9DL (\*) Notice: Subject to any disclaimer, the term of this patent is extended or adjusted under 35 U.S.C. 154(b) by 0 days.

This patent is subject to a terminal disclaimer.

(21) Appl. No.: 07/720,777

(22) PCT Filed: Aug. 21, 1989

(86) PCT No.: PCT/GB89/00972

§ 371 (c)(1),
(2), (4) Date: Nov. 21, 1994

(87) PCT Pub. No.: WO90/07912

PCT Pub. Date: Jul. 26, 1990

(65) Prior Publication Data

US 2001/0041321 A1 Nov. 15, 2001

(30) Foreign Application Priority Data

Jan. 16, 1989 (GB) .............................................. 8900896

(51) Int. Cl.[7] .............................................. A61C 17/00
(52) U.S. Cl. .............................................. 433/80; 433/127
(58) Field of Search .......................... 433/80, 126, 127, 433/128

(56) References Cited

U.S. PATENT DOCUMENTS

| 1,388,312 | A | * | 8/1921 | Seeger | 433/96 |
|---|---|---|---|---|---|
| 1,958,332 | A | * | 5/1934 | Carpenter | 433/80 |
| 3,593,423 | A | | 7/1971 | Jones et al. | 433/80 |
| 3,874,083 | A | | 4/1975 | Buckley | 433/80 |
| 4,026,025 | A | * | 5/1977 | Hunt | 433/80 |
| 4,083,115 | A | * | 4/1978 | McKelvey | 433/96 |
| 4,248,589 | A | * | 2/1981 | Lewis | 433/80 |
| 4,276,880 | A | * | 7/1981 | Malmin | 433/80 |
| 4,531,913 | A | | 7/1985 | Taguchi | 433/80 |
| 4,592,728 | A | * | 6/1986 | Davis | 433/80 |
| 4,619,612 | A | | 10/1986 | Weber et al. | 433/80 |
| 5,033,961 | A | * | 7/1991 | Kandler et al. | 433/80 |
| 5,049,071 | A | * | 9/1991 | Davis et al. | 433/80 |
| 5,433,485 | A | * | 7/1995 | Austin, Jr. et al. | 433/80 |

FOREIGN PATENT DOCUMENTS

| DE | 2548580 | * | 5/1977 |
| EP | 0029636 | | 6/1981 |
| GB | 1049162 | | 11/1966 |
| GB | 2213732 | | 8/1989 |
| JP | 5626415 | | 6/1981 |
| JP | 5910984 | | 4/1984 |

\* cited by examiner

Primary Examiner—John J. Wilson
(74) Attorney, Agent, or Firm—Pearson & Pearson, LLP

(57) ABSTRACT

A dental apparatus having a disposable nozzle tip (11) for a three-way syringe device (12) for spraying air or water. The nozzle tip (11) comprises an assembly of two coaxial tubes (20, 21) which can be readily attached/detached from the syringe device (12), such attachment can be effected directly or via an adaptor (26) which allows the nozzle tip (11) to be connected to a number of different devices. The nozzle tip (11) is constructed from a plastics material which facilitates disposability.

15 Claims, 2 Drawing Sheets

DENTAL APPARATUS

This application was the National Stage of International Application No. PCT/GB89/00972, filed Aug. 21, 1989, which claimed priority of Great Britain patent application Ser. No. 8900896.5, filed Jan. 16, 1989.

TECHNICAL FIELD

This invention relates to dental apparatus, and in particular to syringe apparatus for providing a jet of air, liquid or air/liquid mixture to a patient undergoing dental treatment.

BACKGROUND ART

Such three-ay syringe apparatus is used for cleaning the mouth of dust and small particles of tooth or filling material after drilling, grinding, scraping or the like. The apparatus comprises a hand-held appliance to which a supply of air and a supply of water, both under pressure, are supplied, and has a nozzle assembly or nosel tip at the operating end thereof. Such nozzle assembly or nosel tip comprises a coaxial tube assembly which is secured on the end of the three-way syringe apparatus. Both inner and outer tube of the nosel tip are of metal, for example brass, stainless steel, anodised aluminum or the like, and since the inner tube must be supported within the outer tube whilst allowing flow through the outer tube, the nosel tip is relatively costly to produce. Although the three-way syringe apparatus is not actually intended to come into contact with the patient's mouth, inevitably such contact does occur from time to time since the nosel tip must be placed within the mouth in order that the jet can be directed to the required location. Consequently it is possible for the nosel tip at least to become contaminated during use. Conventionally, the dentist of the dental assistant will clean the nosel tip, after use of the syringe device, by means of cleaning fluid. However, this is not a wholly satisfactory method of ensuring that the nosel tip is contamination-free for the next use. Alternatively, the nosel tip could be removed and autoclaved, but this is a time-consuming operation which is frequently not carried out.

DISCLOSURE OF INVENTION

It is an object of the present invention to provide a dental apparatus of the above described type whereby it is possible to ensure that a contamination-free apparatus is available for each occasion of use.

The invention provides a dental apparatus comprising a nosel tip for a three-way syringe device, the nosel tip comprising a co-axial tube assembly having attachment means adapted for releasable attachment of the nosel tip to a syringe device, wherein at least an outer tube of said co-axial tube assembly is of a plastics material.

By means of the invention the nosel tip can be cheaply produced so that each nosel tip may be removed from the syringe device after use on one patient and discarded, so that a new uncontaminated nossel tip can be attached to the syringe device for use on the next patient. In this way, the risk of cross-infection between patients is avoided or at least substantially reduced.

An inner tube of said coaxial tube assembly may be of metal, for example brass, stainless steel or anodised aluminum. Alternatively the inner tube may also be of a plastics material. The outer tube may be moulded onto the inner tube. The nosel tip may have a cap part which may be secured to or integral with said outer tube and said cap part may have the attachment means formed thereon. Said attachment means may comprise a screw-thread provided internally of the cap part or may comprise bayonet or catch receiving means. The apparatus may also comprise an adaptor, disposed between said nosel tip and syringe device, the adaptor allowing attachment of said nosel tip to the device. Thus in the case where an adaptor is present, it is possible for the same nosel tip to be fitted to different syringe devices by the use of different adaptors, said adaptor may have a cap part with a screw-thread attachment means provided internally thereof, and a screw-thread for engagement with the nosel tip or a bayonet or catch means adapted to be received in bayonet or catch receiving means on the nosel tip.

The adaptor may be arranged to cooperate with the nosel tip via securing means, the securing means providing a leak-proof connection between the nosel tip and adaptor. Preferably the adaptor has a recess therein in which one end of said securing means locates. In this case a seal may be provided to secure and seal the end of said securing means in the recess. The seal may be an 'O' ring or rubber seal or the like. The other end of said securing means may have a plurality of flanges extending radially outward thereof, the flanges locating in grooves provided in said nosel tip. Preferably there are four such flanges spaced angularly by 90° around the outer surface of said other end of the securing means.

BRIEF DESCRIPTION OF DRAWINGS

The invention will now be described with reference to the accompanying drawings, in which.

BEST MODES FOR CARRYING OUT THE INVENTION

Figure 1:
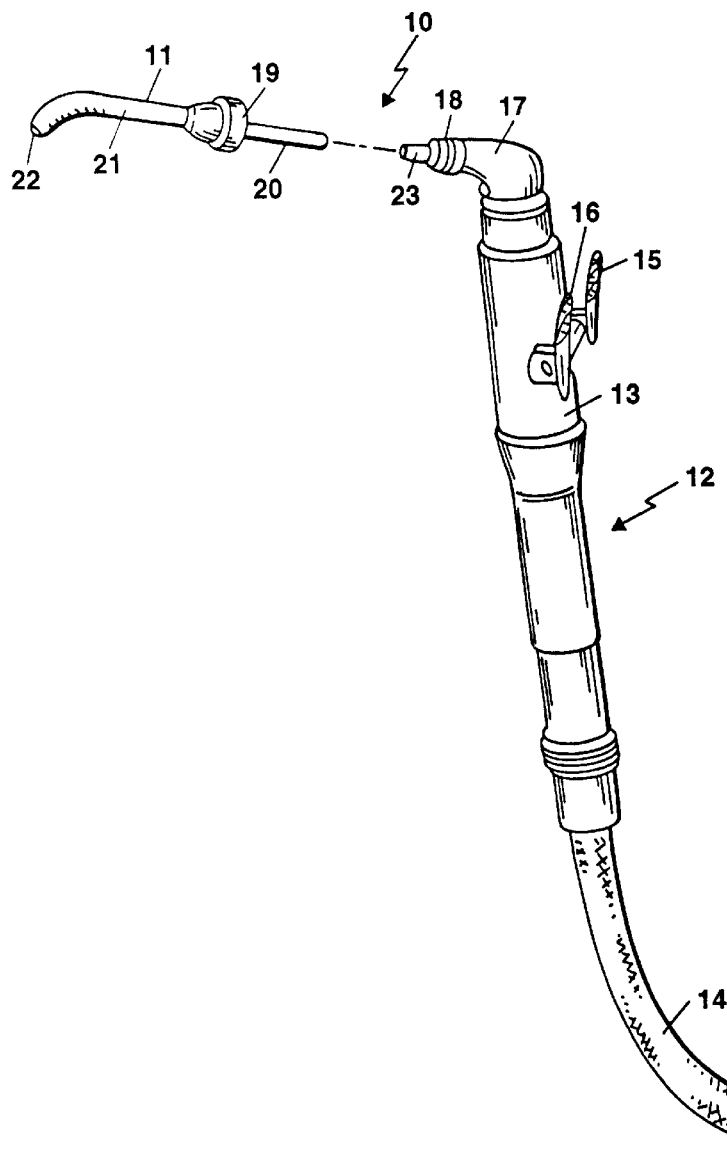
FIG. 1 is an elevation of a first embodiment.

Referring now to FIG. 1 there is shown a dental apparatus 10 comprising a nosel tip 11 for a three-way syringe device 12. The syringe device 12 comprises a body 13 which is connected to a flexible coaxial pipe arrangement 14, itself connected to sources (not shown) of air and water under pressure. Two levers 15, 16 are provided on the body 13 and are operable to allow flow of air, water or air and water through the apparatus 10. The syringe device 12 has a head 17 which is provided with a male screw-threaded portion 18, and the nosel tip 11 has a cap part 19 having an internal screw-thread (not shown), by means of which screw-threads the nosel tip 11 can be removably attached to the head 17.

The nosel tip 11 comprises an inner tube 20 and an outer tube 21 which form a coaxial tube assembly from the cap part 19 to the twin jet end 22. The inner tube 20 extends beyond the cap part 19 so as to be sealingly received in a co-operating inner tube 23 of the head 17. This ensures that there is no back flow of one fluid medium down the supply pipe of the other fluid medium when the latter is not being used.

The inner tube 20 may be of any suitable material such as brass, stainless steel or anodised aluminium, or a plastics material. However, the outer tube 21 is of a plastics material and may be moulded, integrally with the cap part 19, onto the inner tube 20. By this means the nosel tip 11 can be inexpensively produced so that it can be discarded after use of the apparatus 10 on one patient to reduce the risk of cross-inflection of a subsequent patient. A new uncontaminated nosel tip 11 is readily attached to the head 17 for use of the apparatus 10 on another patient.

Figure 2:
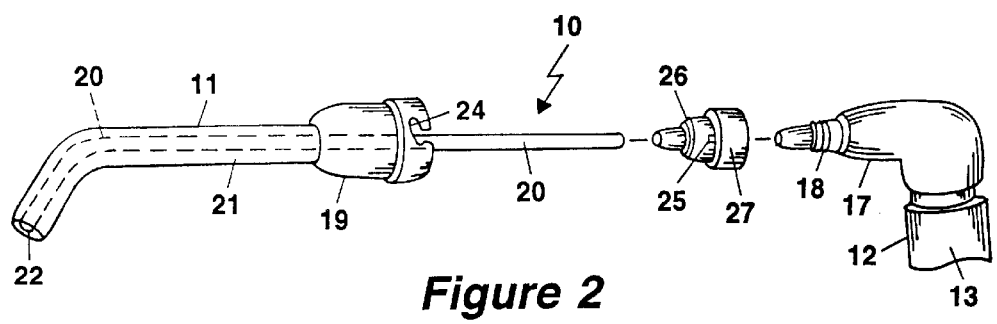
FIG. 2 is an exploded elevation of a second embodiment.

As an alternative to the cap part 19 being provided with an internal screw thread, it may be provided with bayonet receiving means 24 in the form of one or more L-shaped slots as shown in FIG. 2. In all other respects the nosel tip 11 shown in FIG. 2 is identical with that shown in FIG. 1. The head 17 of the syringe device 12 may be provided with bayonets 25 adapted to be received in the bayonet receiving means 24 of the nosel tip 11. Alternatively, as shown in FIG. 2, the head 17 may be provided with the conventional male screw-threaded portion 18 and an adapter 26 is provided. The adaptor 26 has bayonets 25 thereon and an internally screw-threaded cap part 27 so that it may be attached to a conventional syringe device 12 and the nosel tip 11 may be readily attached and removed from the adaptor 26 by cooperation of the bayonets 25 and the bayonet receiving slots 24. Other readily separable attachment means will be readily apparent to persons skilled in the art. For example, bayonets 25 and slots 24 may be replaced by a radially outward spring loaded catch which is received in an aperture or outwardly directed recess in the cap part 19, or an internal bore of the cap part 19 may be dimensioned so that the cap part is simply a push fit on a shoulder of the adaptor 26.

Figure 3:
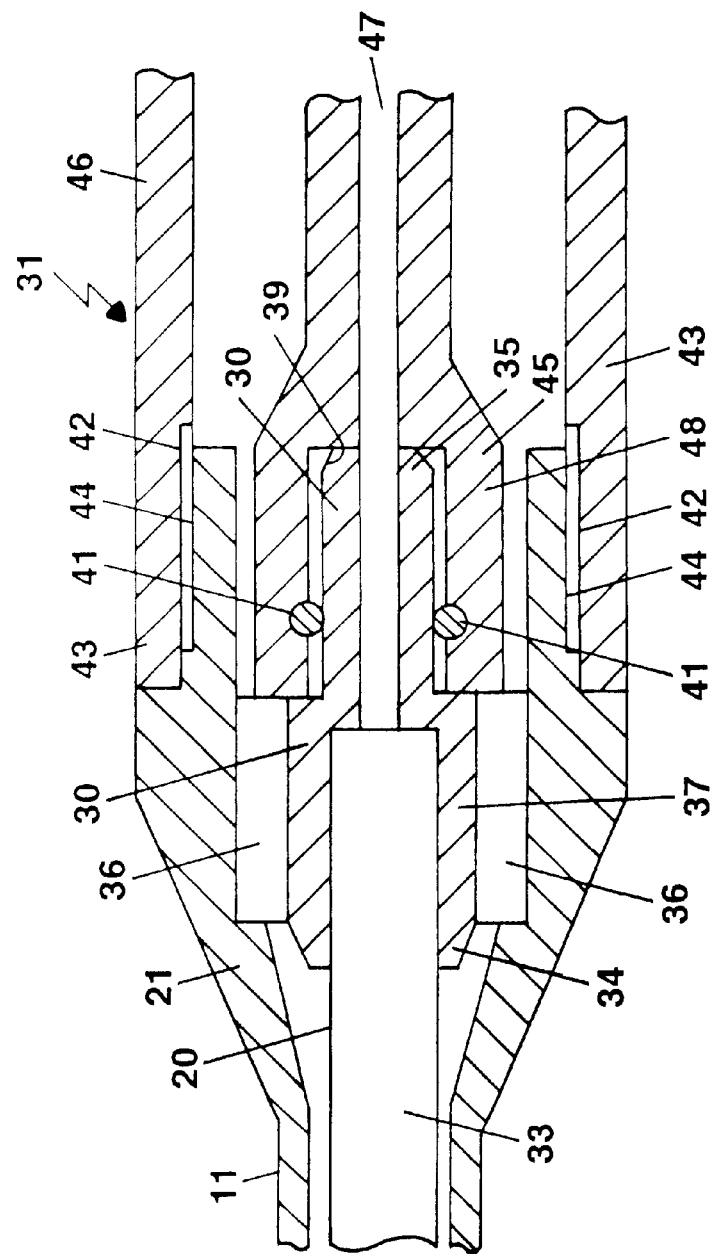
FIG. 3 is a sectional side view of part of a third embodiment showing the region of connection between the adaptor and the nosel tip.

A further alternative is shown in FIG. 3 in which a securing means 30 is used to locate an adapter 31 generally similar to that shown as 26 in FIG. 2, relative to the inner tube 20 of the nosel tip 11. The securing means is of the form of a stepped hollow body 30 having a stepped bore 33 thereto. In the embodiment shown the body 30 is a generally cylindrical form, however other shapes may be used as appropriate. Both ends 34 and 35 of the body 30 are tapered to allow easy fitting of the structure. A number of flange structures 36 protrude radially outwardly from the enlarged part 37 of the body 30 which locate in internal grooves (not shown) in the outer tube 21, fixing the two parts relative to each other. Preferably four such flanges 36 protrude from the body 30 and are spaced angularly by 90°. The reduced part 38 of the body 30 is arranged to cooperate with a recess 39 in the adaptor 31 in any suitable manner, for example by a push fit and is sealed therein by way of seal 41.

The adaptor comprises a stepped inner retaining structure 45 having a stepped axial bore 47 and an outer sleeve 46 formed integrally therewith. The recess 39 is provided in a part 48 of the structure 45 and is arranged to engage with the inner tube 20 via the securing means 30 in sealing relationship thereto providing a continuous bore for the flow of fluid. The outer sleeve 46 has internal screw-threads 42 on one end 43 thereof which engage with corresponding screw-threads 44 on the external surface of the nosel tip 11, providing a further continuous bore between the inner retaining structure 45 and the outer sleeve 46.

With this arrangement it is possible to provide a nosel tip which is both hygienic in that it is readily removable and disposable and can be fitted securely to the apparatus.

It is of course to be understood that the invention is not intended to be restricted to the details of the above embodiment which are described by way of example only.

What is claimed is:

1. Dental apparatus comprising a syringe tip for a three-way syringe device having a connector for attachment thereto of said tip, said tip comprising a coaxial assembly of an inner tube and an outer tube and having thereon attachment means adapted for releasable attachment of said tip to said syringe device by interlocking interengagement of said attachment means with a cooperable structure, wherein an adaptor is provided with said cooperable structure thereon whereby said attachment means is adapted for said releasable attachment via said adaptor disposed between said tip and said connector of said syringe device, and that said outer tube of said coaxial tube assembly is of plastics material and said inner tube of said coaxial assembly is of metal, whereby said tip is formed as a removable and disposable part.

2. Dental apparatus comprising a syringe tip for a three-way syringe device having a connector for attachment thereto of said tip, said tip comprising a coaxial assembly of an inner tube and an outer tube and having thereon attachment means adapted for releasable attachment of said tip to said syringe device by interlocking interengagement of said attachment means with a cooperable structure, wherein an adaptor is provided with said cooperable structure thereon whereby said attachment means is adapted for said releasable attachment via said adaptor disposed between said tip and said connector of said syringe device, and that at least said outer tube of said coaxial tube assembly is of plastics material, whereby said tip is formed as a removable and disposable part; and said adaptor is arranged to cooperate with said tip via securing means, said securing means providing a leak-proof connection between said tip and said adaptor wherein the other end of said securing means has a plurality of flanges extending radially outward thereof, said flanges locating in corresponding grooves provided in said nozzle tip.

3. Apparatus according to claim 2 wherein said other end of said securing means is provided with four of said plurality of flanges spaced angularly by 90 degrees around its external periphery.

4. Dental apparatus comprising a syringe tip for a three-way syringe device having a connector for attachment thereto of said tip comprising a coaxial assembly of an inner tube and an outer tube and having thereon a cap part with attachment means adapted for releasable attachment of said tip to said syringe device by interlocking interengagement of said attachment means with a cooperable structure, said inner tube extending into said cap part and said cap part being formed integrally with said outer tube, wherein an adaptor is provided with said cooperable structure thereon whereby said attachment means is adapted for releasable attachment via said adaptor disposed between said tip and said connector of said syringe device with said cap part and inner tube engaged with said adaptor, and that at least said outer tube of said coaxial tube assembly is of plastics material, whereby said tip is formed as a removable and disposable part.

5. Apparatus according to claim 4 wherein said inner tube is fabricated from plastics material.

6. Apparatus according to claim 4 wherein said outer tube is molded onto said inner tube.

7. Apparatus according to claim 4 wherein said cap part has said attachment means formed thereon.

8. Apparatus according to claim 4 wherein said attachment means comprises a screw-thread provided internally of said cap part.

9. Apparatus according to claim 4 wherein said attachment means comprises bayonet or catch receiving means.

10. Apparatus according to claim 4 wherein said adaptor is arranged to cooperate with said tip via securing means, said securing means providing a leak-proof connection between said tip and adaptor.

11. Apparatus according to claim 10 wherein said adaptor has a recess therein, in which one end of said securing means locates.

12. Apparatus according to claim 11 wherein said one end of said securing means is retained within said recess by way of a seal.

13. Apparatus according to claim 12 wherein said seal comprises an 'O' ring.

14. Apparatus according to claim 10 wherein the other end of said securing means has a plurality of flanges extending radially outward thereof, said flanges locating in corresponding grooves provided in said nozzle tip.

15. Apparatus according to claim 14 wherein said other end of said securing means is provided with four said flanges spaced angularly by 90° around its external periphery.

* * * * *